United States Patent [19]

Green

[11] Patent Number: 4,819,853
[45] Date of Patent: Apr. 11, 1989

[54] SURGICAL FASTENER CARTRIDGE

[75] Inventor: David T. Green, Westport, Conn.
[73] Assignee: United States Surgical Corporation, Norwalk, Conn.
[21] Appl. No.: 140,030
[22] Filed: Dec. 31, 1987
[51] Int. Cl.$^4$ ............................................ A61B 17/00
[52] U.S. Cl. ................................ 227/19; 227/DIG. 1
[58] Field of Search ........................... 227/19, DIG. 1
[56] References Cited

U.S. PATENT DOCUMENTS 4,290,542  9/1981  Fedotou et al. .............. 227/DIG. 1
4,665,916  5/1987  Green .......................... 227/DIG. 1

Primary Examiner—Paul A. Bell
Attorney, Agent, or Firm—Dilworth & Barrese

[57] ABSTRACT

A surgical fastener apparatus possesses an improved fastener cartridge component. The cartridge includes a fastener holder pivotally connected to an anvil assembly, there being defined upon the opposed surfaces of said holder and anvil, gripping means for taking up the pulling and preventing or impeding such force from working against the fastener line.

9 Claims, 4 Drawing Sheets

SURGICAL FASTENER CARTRIDGE

BACKGROUND OF THE INVENTION

This invention relates to a surgical fastener cartridge adapted for use with an actuator apparatus for simultaneously applying a plurality of surgical fasteners to body tissue.

Surgical stapling apparatus in which a plurality of surgical fasteners are applied substantially simultaneously to produce an array of surgical fasteners are known. Typically, these apparatus include a fastener holder disposed on one side of the tissue to be fastened, an anvil assembly parallel to the fastener holder on the other side of the tissue to be fastened, means for linearly translating the fastener holder and the anvil assembly toward one another so that the tissue is clamped between them, and means for driving the fasteners from the fastener holder so that the ends of the fasteners pass through the tissue and form finished fasteners as they make contact with the anvil assembly, thereby producing an array of finished fasteners in the tissue. The term "fasteners" is used herein as a generic term for metal surgical staples, the staple-shaped portion of two-part resinous surgical fasteners, and their equivalents. Similarly, the term "anvil assembly" is used herein as a generic term to include the anvil used to clinch metal surgical staples, the retainer holder and retainer member of two-part resinous surgical fasteners, and the equivalent of these elements.

In common use are apparatus in which the fastener holder and anvil assembly comprise a disposable cartridge removably mounted in or on a permanent actuator for supporting and actuating the cartridge. The cartridge is disposable after a single use. The permanent actuator is reusable in the same surgical procedure after reloading with a fresh cartridge, and is reusable in another surgical procedure after cleaning, sterilizing, and reloading. Also available are disposable surgical apparatus, in which the cartridge and actuator are preassembled, ready for use, and are then disposed of after a single use.

Although instruments of the type described above are available for performing several different types of surgical stapling procedures requiring instruments and staple arrays of various configurations, an illustrative type of instrument is the so-called thoracic-abdominal surgical stapler, which is typically used for forming a row of staples laterally through hollow body organs such as the thorax, trachea, stomach, uterus or intestines.

U.S. Pat. No. 4,665,916, the contents of which are incorporated by reference herein, describes a surgical stapler apparatus of the foregoing type featuring a fastener cartridge of improved design and operation. The cartridge includes an alignment pin to achieve and maintain proper relative positioning of the fastener holder and anvil components thereof. When it is about to be actuated, the surgical stapler of U.S. Pat. No. 4,665,916 is positioned in such a way that tissue to be stapled is clamped in place between the fastener-ejecting surface of the holder and the surface of the anvil. Clamping pressure exerted against both sides of the tissue is sufficient to provide effective hemostasis along two linear sites which, upon actuation ("firing") of the instrument, receive parallel rows of staples on either side of an incision formed by tissue cutting means, also incorporated in the holder, whose deployment is mechanically synchronized to immediately follow the insertion of the fasteners. The magnitude of this clamping pressure is not so great, however, as to cause irreversible tissue trauma (necrosis).

In a Cesarean birth, a fetus is delivered by surgery which requires an incision through the uterus (hysterotomy). Because of the blood-rich nature of uterine tissue, it is especially important to achieve rapid and effective hemostasis for the length of the incision. However, due to the stretched, or taut, condition of the uterine wall at the time a Cesarean sectioning is performed, there is a tendency when employing conventional surgical instruments similar to that of U.S. Pat. No. 4,665,916 for the tissue to pull away from the fasteners after the incision is formed. Any actual pulling away of tissue from the fasteners poses the risk of substantial damage to the tissue in this region.

It is therefore an object of the present invention to provide a surgical stapler which minimizes or eliminates the possibility of tissue pulling away from the fasteners after the latter are positioned in place and the incision is made and until clamping pressure is released.

It is a particular object of the invention to provide a fastener cartridge which transfers the pulling tendency of tissue which is under tension away from the fastener line to a site which is remote therefrom.

SUMMARY OF THE INVENTION

By way of realizing the foregoing and other objects of the invention, there is provided an improved surgical fastener cartridge for use with an actuator assembly including a rigid frame having a generally U-shaped portion for applying rows of surgical fasteners to body tissue and forming an incision in the tissue between said rows, said cartridge possessing an anvil assembly;

a fastener holder pivotally connected to the anvil assembly adjacent one end of the anvil assembly, the fastener holder containing a plurality of surgical fasteners and including fastener driving means for substantially simultaneously driving all of the fasteners from the fastener holder;

means associated with the anvil assembly for allowing the cartridge to be removably mounted on the actuator frame so that the anvil assembly is adjacent a first leg of the U-shaped portion, so that the pivotal connection between the anvil assembly and the fastener holder is adjacent the base of the U-shaped portion, and so that the fastener holder is adjacent a second leg of the U-shaped portion, the fastener holder being movable relative to the frame when the cartridge is thus mounted on the frame so that when the fastener holder is pivoted away from the anvil assembly, the tissue to be fastened can be positioned between the anvil assembly and the fastener holder via the open side of the U-shaped portion;

spacer means located adjacent the side of the cartridge opposite the pivotal connection between the anvil assembly and the fastener holder for maintaining a predetermined minimum spacing between the anvil assembly and the fastener holder when the fastener holder is pivoted toward the anvil assembly; and, knife means for cutting the tissue clamped between the fastener holder and the anvil assembly, the improvement comprising tissue gripping means associated with the fastener holder, said gripping means being positioned parallel to, and away from, rows of fastener-containing apertures such that during use, said tissue gripping means receives the pulling force of the clamped tissue and prevents or impedes such force from being exerted against the applied fasteners.

DETAILED DESCRIPTION OF THE DRAWINGS

FIGS. 1A and 1B are, respectively, a perspective view of the surgical stapler apparatus described in U.S. Pat. No. 4,665,916 showing the fastener cartridge component about to be inserted in the actuator component and an enlarged elevational view of a part of the fully assembled apparatus showing tissue clamped and ready to be fastened;

DESCRIPTION OF THE PREFERRED EMBODIMENTS

Figures 1A, 1B:
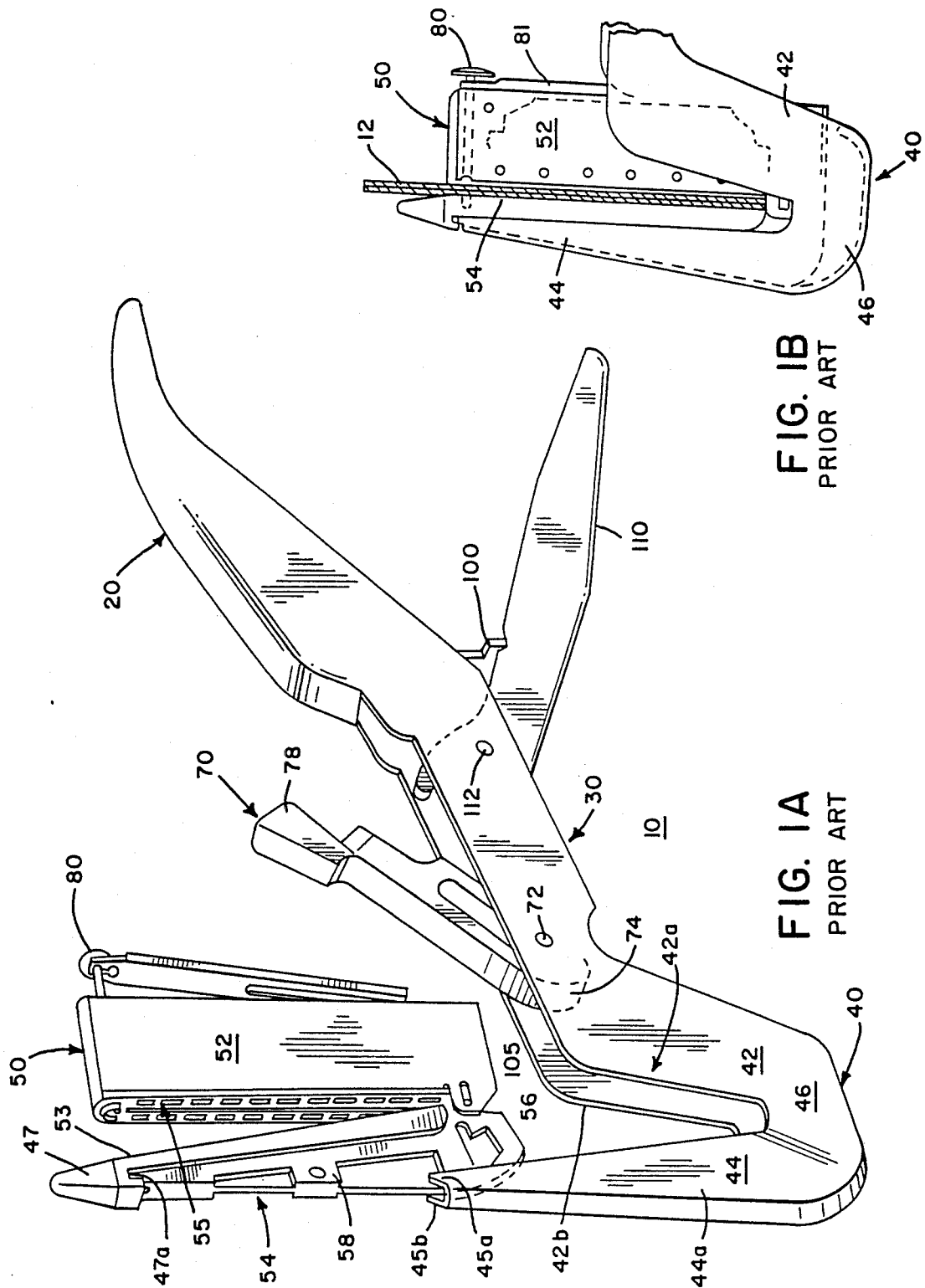

In order to more fully appreciate the advance in the art of surgical fastener apparatus, and in particular the fastener cartridge component thereof, embodied in the present invention, FIGS. 1A and 1B are presented by way of illustrating a prior art instrument, more fully described in U.S. Pat. No. 4,665,916, over which the invention herein represents a significant improvement.

As shown in FIGS. 1A and 1B, the aforesaid prior art surgical fastener instrument includes a handle 20 adjacent the proximal end of the instrument, a longitudinal connecting structure 30 and an open U-shaped or V-shaped support structure 40 at the distal end of connecting structure 30. Support structure 40 comprises a proximal leg 42, a distal leg 44, and a base 46 joining one end of each of legs 42 and 44. Support structure 40 lies in a plane substantially parallel to the longitudinal axis of connecting structure 30. In use, the instrument is positioned relative to tissue 12 to be fastened so that the tissue is generally between legs 42 and 44 and transverse to the plane of support structure 40.

Disposable cartridge 40, shown in FIG. 1A about to be inserted within leg 44 of support structure 40 and in FIG. 1B, fully seated within said structure, includes fastener holder 52 and anvil assembly 54. Anvil assembly 54 is mounted into distal leg 44 and fastener holder 52 is mounted into proximal leg 42. The end of cartridge 50 at which pivotal axis 56 is located is inserted into base 46. Pivotal axis 56 allows pivotal motion of fastener holder 52 and anvil assembly 54 relative to each other and, together with slots 105, also allows a limited amount of motion of the fastener holder perpendicular to anvil assembly surface 53.

Anvil assembly 54 is designed to slide longitudinally into and out of leg 44 of support structure 40. The distal side of anvil assembly 54 has a distally projecting retaining structure 58 which fits between plates 44a and 44b of distal leg 44. Cartridge 50 is releasably retained to leg 44 by a friction fit between retaining structure 58 and plates 44a and 44b, and is positioned accurately in the longitudinal direction on leg 44 by the fit between projections 45a and 45b and cutouts 47a and 47b (not shown) at the corresponding ends of anvil assembly 54. When cartridge 50 is positioned in support structure 40 and projections 45a and 45b are located against cutouts 47a and 47b, anvil assembly 54 will be located between plates 42a and 42b of proximal leg 42.

Figure 2:
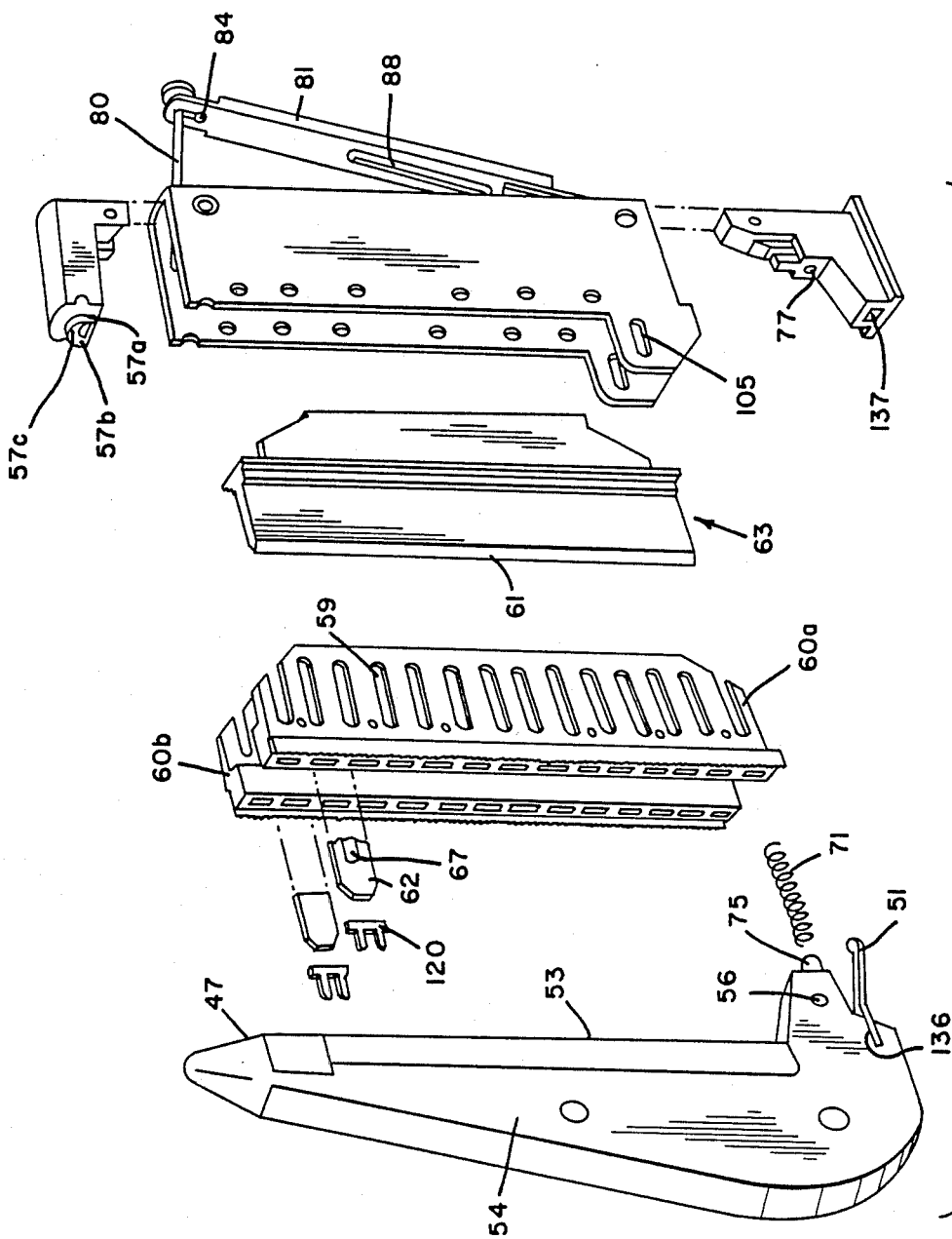
FIG. 2 is an exploded perspective view of the improved fastener holder of the present invention.
Figure 4:
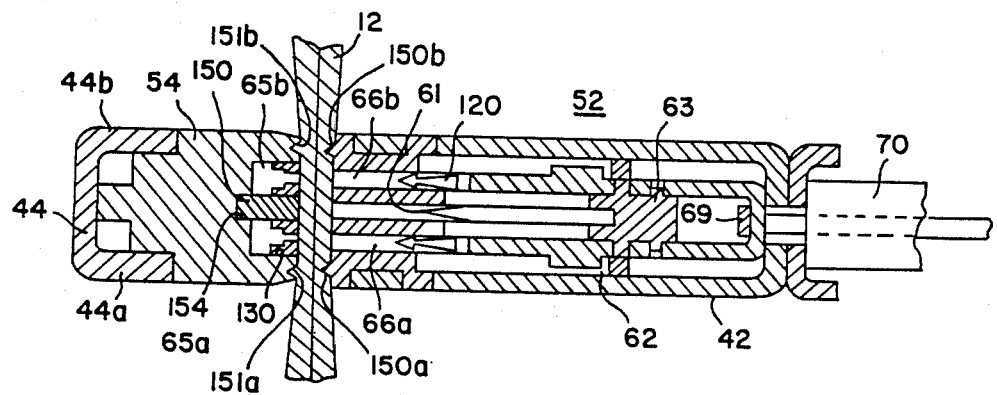
FIG. 4 is a top sectional view of the fastener holder of FIG. 3 showing the condition of the apparatus with the tissue clamped and engaged by the tissue gripping means and ready to be fastened and cut; and, FIG. 5 is a top sectional view of a portion of the fastener holder of FIG. 4 showing an alternative tissue gripping arrangement.

Disposable cartridge 50 of FIGS. 1A and 1B together with pivotally mounted anvil assembly 54, as well as the features which are proper to the device of the present invention, are shown in detail FIG. 4. Anvil assembly 54 has two parallel rows of retainer-containing apertures 65a and 65b which are respectively aligned with two rows of fastener-containing apertures 66a and 66b located in fastener holder 52. Each fastener containing aperture initially contains one fastener 120, and each retainer-containing aperture initially contains one retainer 130. The apertures are further aligned so that one retainer in the associated row of retainers is opposite one fastener in the associated row of fasteners. The two prongs of the fastener are aligned with the two apertures in the retainer. Behind each fastener is a fastener pusher 62 slidably mounted in pusher holders 60a and 60b (see FIG. 2). During ejection of the fasteners, the proximal ends of fastener pushers 62 all contact knife-fastener pusher member 63 which also is slidably mounted in fastener holder 52. As seen in FIG. 2, fastener pushers 62 are guided along in the distal direction by slots 59 in pusher holders 60a and 60b into which projections 67 of fastener pushers 62 extend. Access to knife-fastener pusher member 63 is through an elongated slot in the proximal side of fastener holder 52 and elongated slot 88 in spring 81, to be discussed in more detail below. Fastener holder 52 normally is biased away from anvil assembly 54 by leaf spring 51 and spring 71. One end of leaf spring 51 is mounted in tongue 136 in anvil assembly 54. The other end of leaf spring 51 bears against surface 137 inside fastener holder 52. Spring 71 biases pivotal axis 56 to the distal end of slots 105, and is kept in place by projection 75 and cylindrical space 77.

Figure 3A:
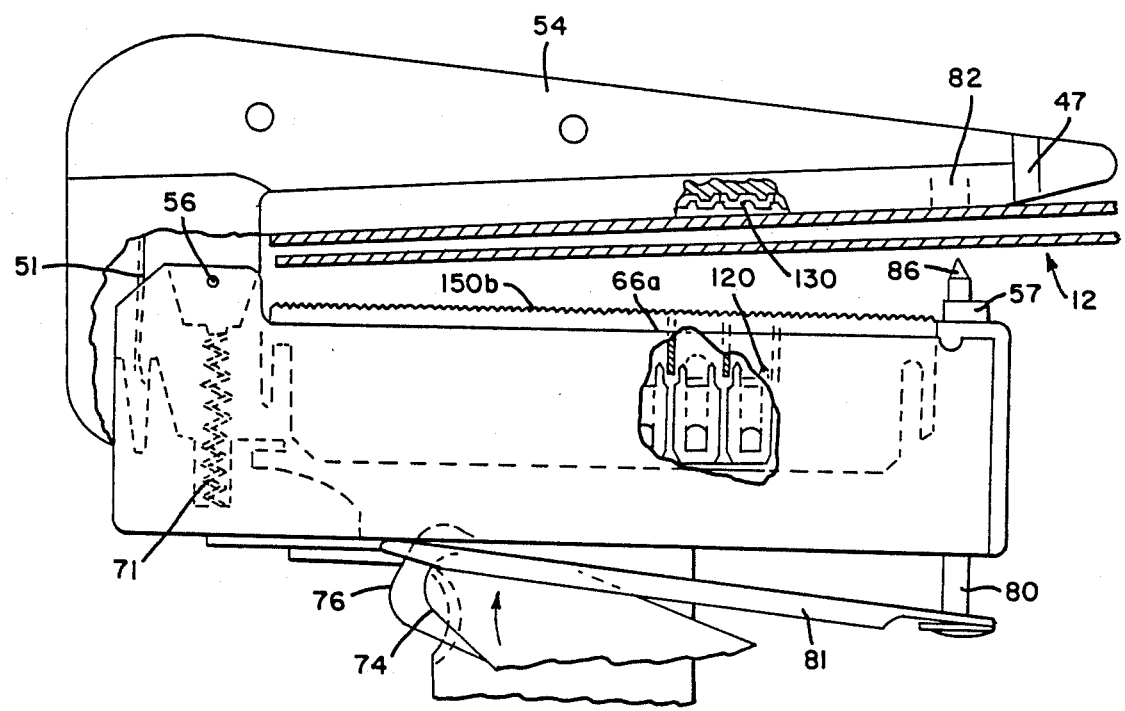
FIG. 3A is an enlarged elevational sectional view of a part of the fastener holder of FIG. 2 illustrating the operation of the device in clamping and gripping the tissue to be fastened and cut.
Figure 3B:
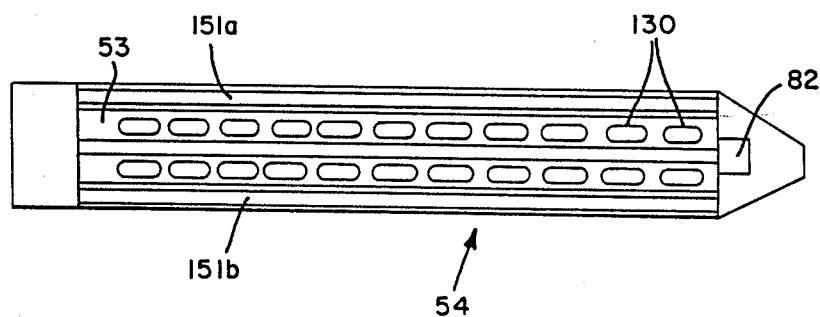
FIG. 3B is a plan view of the fastener-receiving surface of the anvil element shown in FIG. 2A.

Fastener holder 52 also carries alignment pin 80. In order to prevent the end of alignment pin 80 from partly obstructing the open end of cartridge 50 when that cartridge is open, and thereby presenting a possible hazard to the tissue being placed in or removed from the instrument, alignment pin 80 is reciprocally mounted in fastener holder 52 and provided with means for automatically extending the pin during the stapling operation and automatically retracting the pin when cartridge 50 is opened. As shown, for example, in FIG. 2, the proximal end of pin 80 is engaged by the slotted end 84 of leaf spring 81 which extends along the proximal side of fastener holder 52 and is anchored at the bottom of fastener holder 52. Leaf spring 81 has an elongated slot 88 which is generally co-extensive with a slot in fastener holder 52. Leaf spring 81 is arranged so that it is normally inclined away from the proximal side of fastener holder 52 in the direction toward pin 80. In this condition, spring 81 holds pin 80 in the retracted position so that distal end 86 of pin 80 does not project from fastener holder 52. As shown in FIG. 3A, distal end 86 of alignment pin 80 is conically-shaped. This enable alignment pin 80 to pierce tissue 12 as the pin is extended beyond fastener holder surface 55 during the stapling operation.

When tissue 12 is in place between fastener holder 52 and anvil assembly 54, pivoting clamp actuator 70 is pivoted clockwise about its pivotal axis 72 causing camming surface 74 on the distal end of actuator 70 to pivot fastener holder 52 counterclockwise about its pivotal axis 56 thereby gradually clamping tissue 12 between fastener holder 52 and opposing anvil assembly surface 53.

When actuator 70 has been fully pivoted clockwise so that it is substantially parallel to the longitudinal axis of connecting structure 30 as shown in FIG. 1B, tissue 12 is then firmly clamped between anvil assembly surface 53 and opposing fastener holder surface 55. As fastener holder 52 closes on tissue 12, alignment pin 80 pierces the tissue and spacer member 57 displaces the tissue surrounding pin 80 and contacts anvil assembly surface 53. Elongated apertures 105 allow pivotal axis 56 to translate linearly in the proximal direction by a small amount as indicated by the arrow in FIG. 3A thereby resulting in fastener holder surface 55 and anvil assembly surface 53 being parallel and ready for firing of fasteners 120.

As fastener holder 52 is pivoted counter-clockwise by actuator 70, the tissue that would otherwise prevent spacer member 57 from contacting anvil assembly surface 53 is displaced by sloping surfaces 57a and 57b of spacer member 57. These surfaces slope towards each other to form a knife-like edge to displace the tissue and act to permit furthest-most projection, i.e., surface 57c of spacer member 57, to abut against anvil assembly surface 53. Proper alignment of fastener holder 52 and anvil assembly 54 is aided by alignment pin 80 which extends through the side of fastener holder 52 opposite pivotal axis 56 and into alignment pin apertures 82 in anvil assembly 54 as fastener holder surface 55 is pivoted parallel to anvil assembly surface 53. As fastener holder 52 is pivoted counter-clockwise, alignment pin 80 extends past spacer member 57 and makes contact with and pushes through the tissue located in front of the alignment pin aperture 82 in the anvil assembly. As fastener holder 52 continues to pivot counter-clockwise spacer member 57 reaches the tissue and begins to displace the tissue which is now surrounding alignment pin 80. When fastener holder 52 is fully pivoted, spacer member 57 has displaced the tissue so as to abut against anvil assembly surface 53 and ensure parallel alignment between fastener holder surface 55 and anvil assembly surface 53.

As shown in FIG. 3A, when actuator 70 is fully pivoted clockwise, driver 76, which is carried by actuator 70, also is substantially parallel to the longitudinal axis of connecting structure 30. The distal end of driver 76 then extends into the proximal side of fastener holder 52 and is adjacent the proximal surface of knife-fastener pusher member 63 (FIG. 2) in the fastener holder. Safety latch 100 (FIG. IA), which normally keeps actuator lever 110 pivoted clockwise away from handle 30, is now released by pivoting it counter-clockwise. Lever 110 can now be pivoted counter-clockwise about pivotal axis 112 toward handle 20, i.e., by squeezing it toward the handle with the fingers of the hand holding the handle, to actuated the fastener driving mechanism.

When lever 110 is pivoted counter-clockwise as just described, the end of lever 110 inside the proximal end of connecting structure 30 contacts the proximal end 78 of driver 76 and moves driver 76 in the distal direction.

The distal end of driver 76 contacts the proximal surface of knife-fastener pusher member 63, thereby driving member 63 in the distal direction and causing it to drive fasteners 120 out of fastener holder 52, through tissue 12, and into retainers 130 held in anvil assembly 54. Located slightly proximally of the distal end of fasteners 120 is knife surface 61 of knife-fastener pusher member 63 (see FIGS. 2 and 4). After fasteners 120 have begun to pierce tissue 12, knife surface 61 begins to cut the tissue. As lever 110 is squeezed fully in the counter-clockwise direction, fasteners 120 lock into retainers 130 and knife surface 61 completely severs tissue 12.

As shown in FIG. 4, strip 150 of a somewhat flexible, resilient material such as nylon is positioned in the anvil assembly surface 53 parallel to knife surface 61 to provide a surface against which knife surface 61 can act to ensure cutting entirely through tissue 12. Strip 150 is fitted into indent 154 in anvil assembly surface 53.

The joining of the tissue is now complete and all that remains to be done is to remove the fastened tissue from the instrument. This is accomplished by releasing lever 110 which, because leaf springs 69 biases knife-fastener pusher member 63 in the proximal direction, causes knife-fastener pusher member 63 to retract into fastener holder 52. Actuator 70 is rotated in the counter-clockwise direction and fastener holder 52 pivots clockwise away from anvil assembly 54, in response to the pressure of leaf spring 51. Also, spring 81 biases alignment pin 80 away from anvil assembly 54 and thus retracts pin 80 into fastener holder 52. Tissue 12 can now be readily withdrawn from the instrument. Cartridge 50 is now removed from the instrument by pulling anvil assembly 54 out of distal leg 44. The expended cartridge is discarded and another cartridge is loaded in the instrument if additional tissue fastening is required during the surgical procedure. When the surgical procedure is complete, instrument 10 is cleaned and sterilized to prepare it for use in another surgical procedure.

For many types of surgical procedures where the tissue to be fastened and cut is not under any significant amount of tension, no appreciable degree of pulling force will be exerted against the fasteners as they are inserted in the tissue. It is to be noted that in the instrument of FIGS. 1A and 1B, anvil assembly surface 53 and opposed fastener holder surface 55 are both relatively smooth. Although such smooth surfaces present no disadvantage where non-tensioned tissue is concerned, they can be disadvantageous where, as in a Cesarean sectioning, the tissue, specifically, uterine tissue, is in a stretched or taut condition and exhibits a tendency to pull away from the fastener lines until the clamping force on the tissue is relieved.

In accordance with the present invention, and as shown in the fastener cartridge illustrated in FIGS. 2, 3A, 3B, 4 and 5, where the various elements thereof correspond to like numbered elements shown in FIGS. 1A and 1B, together with the improved features about to be discussed, tissue gripping means are provided which include rows of serrations 150a and 150b, e.g., of pyramidal shape formed on fastener holder surface 55 and positioned externally to fastener-containing apertures 66a and 66b. When tissue 121 is clamped in place as in the manner previously described, continuous tissue-receiving grooves, or channels, 151a and 151b formed on the lateral fastener-receiving surface 53 of anvil assembly 54 and positioned thereon to be directly opposed to rows of serrations 150a and 150b (see FIGS. 3A and 3B) cooperate with said serrations to apply an effective gripping force to the tissue. Thus, for example, in a Cesarean sectioning, the pulling force exerted by the stretched uterine tissue, which in the case of the fastener instrument of U.S. Pat. No. 4,665,916 would act directly against the rows of applied fasteners, is instead exerted against the tissue along the linear sites where is it gripped by the gripping means of the improved fastener holder herein. This arrangement effectively isolates the pulling force of the stretched tissue from the fasteners thereby eliminating damage to the tissue which might otherwise result were the pulling force to work against the fastened area.

Figure 5:
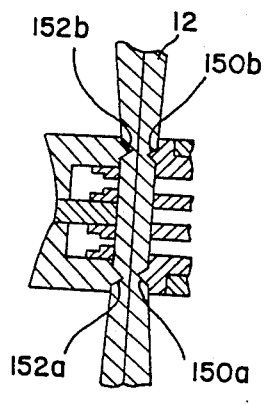

In addition to opposed serrations and grooves, the gripping means of this invention can assume any number of other functionally equivalent configurations. Thus, as shown in FIG. 5, for example, in place of grooves 151a and 151b of FIG. 4, rows of serrations 152a and 152b similar to those of 150a and 150b can be provided. In another alternative embodiment, the gripping function of each of the rows of serrations 150a and 150b can be achieved with continuous gripping elements projecting from the surface of the fastener holder and cooperating with grooves 151a and 151b to provide an effective gripping force against clamped tissue 12.

In still another embodiment, two sets of such continuous gripping elements are provided with one surface projecting from the fastener-ejecting surface of the holder and the other set projecting from the staple-receiving surface of the anvil. As in the case of the serrations/grooves arrangement of FIG. 4, both sets of gripping elements in this further embodiment are positioned externally to the fastener apertures and cooperate to exert the required gripping force against the clamped tissue. If desired, one set of gripping elements can be slightly offset relative to the other set. As is readily apparent, numerous other gripping arrangements are possible.

The location of the cooperating components of the gripping means on one or the other of the opposed anvil and fastener holder surfaces can be the reverse of that described. Thus, e.g., rows of serrations 150a and 150b may be formed on the anvil surface and grooves 151a and 151b may be formed on the fastener holder surface, an arrangement which is opposite that shown in FIGS. 2–4. Whatever the form of the gripping means, it will exert a force against the clamped tissue which is sufficient to prevent or impede the tissue from pulling away from the fastener line but will not be so great as to cause significant injury or trauma to the tissue.

It will be understood that the embodiment shown and described herein is only illustrative of the principles of the invention, and that various modifications can be made by those skilled in the art without departing from the scope and spirit of the invention. In particular, the invention has been described in conjunction with an improved disposable cartridge and a permanent, reusable instrument. The invention could also have been described in conjunction with a totally disposable instrument. When the entire instrument is disposable, as much of the instrument as possible is preferably made of relatively inexpensive materials such as plastic or the like. Preferably only those parts of the instrument which are subject to high stresses are made of metal.

What is claimed is:

1. In a surgical fastener cartridge which is adapted for use with an actuator apparatus having a rigid frame and a generally U-shaped portion for receiving the fastener cartridge, the actuator apparatus actuating the fastener cartridge to form an incision in body tissue and to apply rows of fasteners to the tissue on both sides of the incision, the fastener cartridge including:
   (a) a fastener holder containing a quantity of fasteners, the fasteners being driven, upon actuation of the fastener cartridge, through substantially parallel rows of apertures defined upon a fastener ejecting surface of the fastener holder;
   (b) an anvil connected to the fastener holder and having a surface opposed to the fastener ejecting surface of the fastener holder and, upon actuation of the fastener cartridge, cooperating therewith to apply substantially parallel rows of fasteners to body tissue positioned between the fastener holder and anvil;
   (c) means for driving the fasteners through the apertures upon actuation of the fastener cartridge;
   (d) a tissue cutting knife, the knife edge of which is recessed within the fastener holder in the non-actuated condition of the fastener cartridge and which, upon actuation of the fastener cartridge, extends beyond a knife slot disposed between the rows of apertures; and,
   (e) means for driving the knife edge of the tissue cutting knife through the knife slot upon actuation of the fastener cartridge, the improvement which comprises:
   (f) at least one pair of substantially continuous tissue gripping elements provided upon the fastener ejecting surface of the fastener holder and/or the anvil surface opposed thereto, the tissue gripping elements being arranged on both sides of the knife slot and being substantially coextensive with, and parallel to, the knife slot such that upon actuation of the fastener cartridge resulting in the formation of an incision in the tissue and application of the fasteners to the tissue on each side of the incision, the tissue gripping elements will apply a substantially continuous gripping force to the tissue preventing or impeding lateral movement of tissue away from the fasteners.

2. The fastener cartridge of claim 1 wherein the tissue gripping elements are provided as rows of serrations upon the fastener ejecting surface of the fastener holder, there being additionally provided a pair of grooves formed upon the surface of the anvil opposed thereto with an individual groove directly opposed to an individual row of serrations, said rows of serrations cooperating with said grooves to augment the gripping force which is applied to the body tissue about to be cut and fastened.

3. The fastener cartridge of claim 2 wherein individual serrations in a row possess a pyramidal shape.

4. The fastener cartridge of claim 2 wherein the tissue gripping elements are also arranged parallel to the rows of apertures with each tissue gripping element in the pair being positioned along the outer side of a row of apertures.

5. The fastener cartridge of claim 1 wherein the tissue gripping elements are provided as rows of serrations upon the surface of the anvil opposed to the fastener ejecting surface of the fastener holder, there being additionally provided a pair of grooves formed upon the fastener ejecting surface of the fastener holder with an individual groove directly opposed to an individual row of serrations, said rows of serrations cooperating with said grooves to augment the gripping force which is applied to the body tissue about to be cut and fastened.

6. The fastener cartridge of claim 5 wherein individual serrations in a row possess a pyramidal shape.

7. The fastener cartridge of claim 5 wherein the tissue gripping elements are also arranged parallel to the rows of apertures with each tissue gripping element in the pair being positioned along the outer side of a rows of apertures.

8. The fastener cartridge of claim 1 wherein the tissue gripping elements are provided as opposed rows of serrations upon both the fastener ejecting surface of the fastener holder and the surface of the anvil opposed thereto, said opposed rows of serrations cooperating with each other to augment the gripping force which is applied to the body tissue about to be cut and fastened.

9. The fastener cartridge of claim 1 wherein the tissue gripping elements are also arranged parallel to the rows of apertures with each tissue gripping element in the pair being positioned along the outer side of a row of apertures.

* * * * *

UNITED STATES PATENT AND TRADEMARK OFFICE
CERTIFICATE OF CORRECTION

PATENT NO. : 4,819,853
DATED : April 11, 1989
INVENTOR(S) : David T. Green

It is certified that error appears in the above-identified patent and that said Letters Patent is hereby corrected as shown below:

Column 6, Line 62, "121" should read --12--;

Column 7, bridging Lines 6 and 7, "is it" should read --it is--;

Column 9, Line 6, "rows" should read --row--.

Signed and Sealed this

Twenty-third Day of January, 1990

Attest:

JEFFREY M. SAMUELS

Attesting Officer     Acting Commissioner of Patents and Trademarks